United States Patent
Satyaraj

(12) 
(10) Patent No.: US 10,010,566 B2
(45) Date of Patent: Jul. 3, 2018

(54) COMPOSITIONS AND METHODS USEFUL FOR AMELIORATING AGE RELATED MALADIES

(75) Inventor: Ebenezer Satyaraj, Wildwood, MO (US)

(73) Assignee: NestecSA, Vevey (CH)

( * ) Notice: Subject to any disclaimer, the term of this patent is extended or adjusted under 35 U.S.C. 154(b) by 8 days.

(21) Appl. No.: 14/004,947

(22) PCT Filed: Mar. 12, 2012

(86) PCT No.: PCT/US2012/028712
§ 371 (c)(1),
(2), (4) Date: Sep. 13, 2013

(87) PCT Pub. No.: WO2012/128982
PCT Pub. Date: Sep. 27, 2012

(65) Prior Publication Data
US 2014/0004205 A1 Jan. 2, 2014

Related U.S. Application Data

(60) Provisional application No. 61/465,404, filed on Mar. 18, 2011.

(51) Int. Cl.
| | | |
|---|---|---|
| A61K 35/60 | (2006.01) | |
| A61K 45/06 | (2006.01) | |
| A61K 31/202 | (2006.01) | |
| A61K 31/616 | (2006.01) | |
| A61K 35/20 | (2006.01) | |
| A61K 31/198 | (2006.01) | |
| A61K 31/381 | (2006.01) | |
| A61K 31/385 | (2006.01) | |
| A61K 31/675 | (2006.01) | |
| A23K 20/105 | (2016.01) | |
| A23K 20/147 | (2016.01) | |
| A23K 20/158 | (2016.01) | |
| A23K 50/40 | (2016.01) | |

(52) U.S. Cl.
CPC ............ *A61K 35/60* (2013.01); *A23K 20/105* (2016.05); *A23K 20/147* (2016.05); *A23K 20/158* (2016.05); *A23K 50/40* (2016.05); *A61K 31/198* (2013.01); *A61K 31/202* (2013.01); *A61K 31/381* (2013.01); *A61K 31/385* (2013.01); *A61K 31/616* (2013.01); *A61K 31/675* (2013.01); *A61K 35/20* (2013.01); *A61K 45/06* (2013.01)

(58) Field of Classification Search
CPC ..... A61K 2121/00; A61K 31/00; A61K 35/60
USPC .......... 424/184.1, 520, 523, 554, 93.41, 725
See application file for complete search history.

(56) References Cited

U.S. PATENT DOCUMENTS

| | | | |
|---|---|---|---|
| 2002/0068365 A1* | 6/2002 | Kuhrts | 436/501 |
| 2002/0119928 A1* | 8/2002 | McAnalley | A23L 33/21 424/535 |
| 2004/0166206 A1 | 8/2004 | Archibald et al. | |
| 2006/0014773 A1* | 1/2006 | McCleary | 514/283 |
| 2007/0060651 A1* | 3/2007 | Larson et al. | 514/560 |
| 2010/0056484 A1 | 3/2010 | Farese | |
| 2010/0093863 A1* | 4/2010 | Moinard | A23L 1/3051 514/563 |
| 2010/0233304 A1* | 9/2010 | Pan | A23D 9/007 424/752 |
| 2010/0316769 A1 | 12/2010 | Czarnecki-Maulden | |

FOREIGN PATENT DOCUMENTS

| | | | |
|---|---|---|---|
| CN | 101433241 A | * | 5/2009 |
| WO | 2007073178 A2 | | 6/2007 |
| WO | 2009088433 A1 | | 7/2009 |
| WO | 2010095926 A1 | | 8/2010 |

OTHER PUBLICATIONS

Szaniszlo et al. "New Insights Into Clinical Trial for Colostrinin in Alzheimer's Disease", The Journal of Nutrition, Health and Aging, vol. 14, No. 3, 2009.*
Lorbach et al. "Physiological Falls Risk Assessment in Older People with Alzheimer's Disease" (Dement Geriatric Cognitive Disord, 2007;24:260-265).*
International Search Report & Written Opinion PCT/US2012/028712 dated Jun. 20, 2012.
Extended European Search Report, EP12760637.4, dated Jul. 21, 2014.
Nyby, Michael D., et al., "Dietary Fish Oil Prevents Vascular Dysfunction and Oxidative Stress in Hyperinsulinemic Rats", American Journal of Hypertension, 2005; 18:213-219.

\* cited by examiner

*Primary Examiner* — Christopher Robin Tate
*Assistant Examiner* — Deborah A Davis
(74) *Attorney, Agent, or Firm* — Ronald A. Burchett; Julie M. Lappin

(57) ABSTRACT

The invention provides methods and compositions useful for ameliorating age related maladies, enhancing and maintaining immune function, enhancing and maintaining cognitive function, enhancing and maintaining muscle strength, enhancing and maintaining balance, and reducing and mitigating oxidative stress in an animal. The compositions comprise a combination of at least two of one or more unsaturated fatty acids (UFA); one or more nitric oxide releasing compounds (NORC); one or more anti-glycation agents; and colostrum, and the methods comprise administering to an animal a therapeutically effective amount of the compositions.

10 Claims, No Drawings

COMPOSITIONS AND METHODS USEFUL FOR AMELIORATING AGE RELATED MALADIES

CROSS REFERENCE TO RELATED APPLICATIONS

This application is a national stage application under 35 USC § 371 of PCT/US2012/028712 filed on Mar. 12, 2012 and claims priority to U.S. Provisional Application No. 61/465404 filed Mar. 18, 2011, the disclosures of which are incorporated herein by this reference.

BACKGROUND OF THE INVENTION

Field of the Invention

The invention relates generally to compositions and methods for ameliorating age related maladies and particularly to compositions comprising at least two of one or more unsaturated fatty acids (UFA); one or more nitric oxide releasing compounds (NORC); one or more anti-glycation agents; and colostrum and their use for ameliorating age related maladies in animals.

Description of Related Art

Aging is often characterized by a decline in physiological and biochemical functions including lowered immunity, decreased cognition, loss of muscle strength, loss of balance, and increased oxidative stress. Increased oxidative stress often initiates a cascade of pathophysiologies such as type II diabetes, Alzheimer's disease; heart disease and lowered immune response. Consequently, aging may lead to several chronic diseases, cancers, increased susceptibility to infections, and increased risk of falling leading to injuries, and can lead to an overall decline in quality of life for the individual.

Cognitive impairment may manifest itself in many ways, e.g., short-term memory loss, diminished capacity to learn, diminished rate of learning, diminished attention, diminished motor performance, and/or dementia, among other indicia. In companion animals, loss of cognition may result in various undesirable behaviors. For example, they may not respond to their name or familiar commands, may get lost or confused even in familiar surroundings, may no longer greet or respond to their owners or visitors, may exhibit diminished daytime activity, may walk in circles, may shun affection, and may lose bladder or bowel control.

Loss of muscle strength contributes to frailty, loss of mobility and loss of independence. Loss of balance disrupts everyday movements like standing and walking, it also increases the likelihood of falling.

Decreased immunity lowers the body's ability to fight off infection. It also lowers the body's tolerance of its own cells thereby leading to an autoimmune disorder. Decreased immunity also leads to slower wound healing and lowers the effectiveness of immunizations. The immune system's ability to detect and correct cell defects also declines, which results in an increase in cancers associated with aging.

Oxidative stress has been implicated in a variety of pathological and chronic degenerative processes including the development of cancer, atherosclerosis, inflammation, neurodegenerative disorders, cataracts, retinal degeneration, reperfusion injury after tissue ischemia, and defense against infection.

Though advances have been made, there remains a need to develop compositions and methods useful for ameliorating age-related maladies, particularly in aging humans and other animals. Compositions and methods for enhancing and maintaining immune function, enhancing and maintaining cognitive function, enhancing and maintaining muscle strength, enhancing and maintaining balance, and reducing and mitigating oxidative stress are also needed. Such therapies would be useful to improve the overall quality of life for all involved. For companion animals, these therapies would lead to improved owner satisfaction and would improve the owner-companion animal bond.

SUMMARY OF THE INVENTION

It is, therefore, an object of the present invention to provide compositions and methods useful for ameliorating age related maladies in an animal.

It is another object of the invention to provide compositions and methods useful for enhancing and maintaining immune function, enhancing and maintaining cognitive function, enhancing and maintaining muscle strength, enhancing and maintaining balance, and reducing and mitigating oxidative stress in an animal.

It is another object of the invention to provide compositions and methods for promoting the health and wellness of animals.

It is yet another object of the present invention to provide compositions and methods for extending the prime years of an animal's life.

One or more of these or other objects are achieved by administering to an animal a therapeutically effective amount of a combination of at least two of: one or more unsaturated fatty acids (UFA); one or more nitric oxide releasing compounds (NORC); one or more anti-glycation agents; and colostrum.

Other and further objects, features, and advantages of the present invention will be readily apparent to those skilled in the art.

DETAILED DESCRIPTION OF THE INVENTION

Definitions

The term "animal" means any animal that has a need for ameliorating age related maladies, including but not limited to, enhancing and maintaining immune function, enhancing and maintaining cognitive function, enhancing and maintaining muscle strength, enhancing and maintaining balance, and reducing and mitigating oxidative stress, including human, avian, bovine, canine, equine, feline, hicrine, lupine, murine, ovine, or porcine animals.

The term "companion animal" means domesticated animals such as cats, dogs, rabbits, guinea pigs, ferrets, hamsters, mice, gerbils, horses, cows, goats, sheep, donkeys, pigs, and the like.

The term "unsaturated fatty acids" or "UFA" means polyunsaturated fatty acids or monounsaturated fatty acids, including monocarboxylic acids having at least one double bond. UFAs include (n-6) fatty acids such as linoleic acid (LA) and arachidonic acid (AA) and (n-3) fatty acids such as eicosapentaenoic acid (EPA), alpha-linolenic acid (ALA), docosapentaenoic acid (DPA) and docosahexaenoic acid (DHA). UFAs also include myristoleic acid, palmitoleic acid, oleic acid, linoleic acid, cis-vaccenic acid, and erucic acid.

The term "fish oil" means a fatty or oily extract, relatively rich in UFA, whether crude or purified, obtained from a sea animal, preferably a cold-water fish such as, but not limited to, salmon, tuna, mackerel, herring, sea bass, striped bass, halibut, catfish, and sardines, as well as shark, shrimp, and clams, or any combination thereof. Fish oil is generally a term of art used by ingredient suppliers and encompasses a range of products of varying UFA content and purity.

The term "nitric oxide releasing compounds" or "NORC" means any compound or compounds that cause or can result in the release of nitric oxide in an animal. Examples of such compounds include L-arginine, L-arginine-containing peptides and proteins, and analogs or derivatives thereof that are known or determined to release nitric oxide, such as arginine alpha-ketoglutarate, GEA 3175, sodium nitroprusside, glyceryl trinitrate, S-nitroso-N-acetyl-penicillamine, nitroglycerin, S-NO-glutathione, NO-conjugated non-steroidal anti-inflammatory drugs (e.g., NO-naproxen, NO-aspirin, NO-ibuprofen, NO-Diclofenac, NO-Flurbiprofen, and NO-Ketoprofen), NO-releasing compound-7, NO-releasing compound-5, NO-releasing compound-12, NO-releasing compound-18, diazenium diolates and derivatives thereof, diethylamine NONOate, and any organic or inorganic compound, biomolecule, or analog, homolog, conjugate, or derivative thereof that causes the release of nitric oxide, particularly "free" NO, in an animal. NORC is also defined to include supplements that can be converted to nitric oxide releasing compounds when metabolized in the body, e.g., citrulline and ornithine.

The term "therapeutically-effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The terms "treating", "treat", and "treatment" embrace both preventative, i.e., prophylactic, and palliative treatment.

The terms "pharmaceutically acceptable" and "nutraceutically acceptable" indicates that the substance or composition must be compatible chemically and/or toxicologically, with the other ingredients comprising a formulation, and/or the mammal being treated therewith.

The term "health and/or wellness of an animal" means the complete physical, mental, and social well being of the animal, not merely the absence of disease or infirmity.

The term "extending the prime" means extending the number of years an animal lives a healthy life and not just extending the number of years an animal lives, e.g., an animal would be healthy in the prime of its life for a relatively longer time.

The term "in conjunction" means that compositions of the invention are administered to an animal (1) together in a food composition or (2) separately at the same or different frequency using the same or different administration routes at about the same time or periodically. "Periodically" means that compositions are administered on a schedule acceptable for specific compounds or compositions. "About the same time" generally means that compositions are administered at the same time or within about 72 hours of each other.

The term "dietary supplement" means a product that is intended to be ingested in addition to a normal animal diet. Dietary supplements may be in any form, e.g., solid, liquid, gel, tablet, capsule, powder, and the like. Preferably they are provided in convenient dosage forms, e.g., in sachets. Dietary supplements can be provided in bulk consumer packages such as bulk powders, liquids, gels, or oils. Similarly such supplements can be provided in bulk quantities to be included in other food items such as snacks, treats, supplement bars, beverages, and the like.

The term "aging" means being of an advanced age such that an animal has reached or exceeded 50% of the average life expectancy for the animal's species and/or breed within such species. For example, if the average life expectancy for a given breed of dog is 12 years, then an "aging animal" within that breed is 6 years old or older.

The term "food" or "food product" or "food composition" means a product or composition that is intended for ingestion by an animal, including a human, and provides nutrition to the animal.

The term "regular basis" means at least monthly dosing with compositions of the present invention and more preferably weekly dosing. More frequent dosing or consumption, such as twice or three times weekly, is preferred in certain embodiments. Still more preferred are regimens that comprise at least once daily consumption, e.g., when compositions of the present invention are a component of a food composition that is consumed at least once daily.

The term "single package" means that the components of a kit are physically associated in or with one or more containers and considered a unit for manufacture, distribution, sale, or use. Containers include, but are not limited to, bags, boxes, cartons, bottles, packages such as shrink-wrap packages, stapled or otherwise affixed components, or combinations thereof. A single package may be containers of individual compositions of the present invention and food compositions physically associated such that they are considered a unit for manufacture, distribution, sale, or use.

The term "virtual package" means that the components of a kit are associated by directions on one or more physical or virtual kit components instructing the user how to obtain the other components, e.g., in a bag or other container containing one component and directions instructing the user to go to a website, contact a recorded message or a fax-back service, view a visual message, or contact a caregiver or instructor to obtain instructions on how to use the kit or safety or technical information about one or more components of a kit.

The dosages expressed herein are in milligrams per kilogram of body weight per day (mg/kg/day) unless expressed otherwise.

All percentages expressed herein are by weight of the total weight of the composition unless expressed otherwise.

As used herein, ranges are used herein in shorthand, so as to avoid having to list and describe each and every value within the range. Any appropriate value within the range can be selected, where appropriate, as the upper value, lower value, or the terminus of the range.

As used herein, the singular form of a word includes the plural, and vice versa, unless the context clearly dictates otherwise. Thus, the references "a", "an", and "the" are generally inclusive of the plurals of the respective terms. For example, reference to "a supplement", "a method", or "a food" includes a plurality of such "supplements", "methods", or "foods." Similarly, the words "comprise", "comprises", and "comprising" are to be interpreted inclusively rather than exclusively. Likewise the terms "include", "including" and "or" should all be construed to be inclusive, unless such a construction is clearly prohibited from the context. Similarly, the term "examples," particularly when followed by a listing of terms, is merely exemplary and illustrative and should not be deemed to be exclusive or comprehensive.

The methods and compositions and other advances disclosed here are not limited to particular methodology, protocols, and reagents described herein because, as the skilled artisan will appreciate, they may vary. Further, the terminology used herein is for the purpose of describing particular embodiments only, and is not intended to, and does not, limit the scope of that which is disclosed or claimed.

Unless defined otherwise, all technical and scientific terms, terms of art, and acronyms used herein have the meanings commonly understood by one of ordinary skill in the art in the field(s) of the invention, or in the field(s) where the term is used. Although any compositions, methods, articles of manufacture, or other means or materials similar or equivalent to those described herein can be used in the practice of the present invention, the preferred compositions, methods, articles of manufacture, or other means or materials are described herein.

All patents, patent applications, publications, technical and/or scholarly articles, and other references cited or referred to herein are in their entirety incorporated herein by reference to the extent allowed by law. The discussion of those references is intended merely to summarize the assertions made therein. No admission is made that any such patents, patent applications, publications or references, or any portion thereof, are relevant, material, or prior art. The right to challenge the accuracy and pertinence of any assertion of such patents, patent applications, publications, and other references as relevant, material, or prior art is specifically reserved.

The Invention

In one aspect, the invention provides compositions useful for ameliorating age related maladies in an animal. The compositions comprise a therapeutically effective amount of a combination of at least two of one or more unsaturated fatty acids (UFA); one or more nitric oxide releasing compounds (NORC); one or more anti-glycation agents; and colostrum.

In one aspect, the invention provides methods for ameliorating age related maladies in an animal. The methods comprise administering to the animal a therapeutically effective amount of a combination of at least two of one or more unsaturated fatty acids (UFA); one or more nitric oxide releasing compounds (NORC); one or more anti-glycation agents; and colostrum.

In one aspect, the invention provides compositions useful for enhancing and maintaining immune function in an animal. The compositions comprise a therapeutically effective amount of a combination of at least two of one or more unsaturated fatty acids (UFA); one or more nitric oxide releasing compounds (NORC); one or more anti-glycation agents; and colostrum.

In one aspect, the invention provides methods for enhancing and maintaining immune function in an animal. The methods comprise administering to the animal a therapeutically effective amount of a combination of at least two of one or more unsaturated fatty acids (UFA); one or more nitric oxide releasing compounds (NORC); one or more anti-glycation agents; and colostrum.

In one aspect, the invention provides compositions useful for enhancing and maintaining cognitive function in an animal. The compositions comprise a therapeutically effective amount of a combination of at least two of one or more unsaturated fatty acids (UFA); one or more nitric oxide releasing compounds (NORC); one or more anti-glycation agents; and colostrum.

In one aspect, the invention provides methods for enhancing and maintaining cognitive function in an animal. The methods comprise administering to the animal a therapeutically effective amount of a combination of at least two of one or more unsaturated fatty acids (UFA); one or more nitric oxide releasing compounds (NORC); one or more anti-glycation agents; and colostrum.

In one aspect, the invention provides compositions useful for enhancing and maintaining muscle strength in an animal. The compositions comprise a therapeutically effective amount of a combination of at least two of one or more unsaturated fatty acids (UFA); one or more nitric oxide releasing compounds (NORC); one or more anti-glycation agents; and colostrum.

In one aspect, the invention provides methods for enhancing and maintaining muscle strength in an animal. The methods comprise administering to the animal a therapeutically effective amount of a combination of at least two of one or more unsaturated fatty acids (UFA); one or more nitric oxide releasing compounds (NORC); one or more anti-glycation agents; and colostrum.

In one aspect, the invention provides compositions useful for enhancing and maintaining balance in an animal. The compositions comprise a therapeutically effective amount of a combination of at least two of one or more unsaturated fatty acids (UFA); one or more nitric oxide releasing compounds (NORC); one or more anti-glycation agents; and colostrum.

In one aspect, the invention provides methods for enhancing and maintaining balance in an animal. The methods comprise administering to the animal a therapeutically effective amount of a combination of at least two of one or more unsaturated fatty acids (UFA); one or more nitric oxide releasing compounds (NORC); one or more anti-glycation agents; and colostrum.

In one aspect, the invention provides compositions useful for reducing and mitigating oxidative stress in an animal. The compositions comprise a therapeutically effective amount of a combination of at least two of one or more unsaturated fatty acids (UFA); one or more nitric oxide releasing compounds (NORC); one or more anti-glycation agents; and colostrum.

In one aspect, the invention provides methods for reducing and mitigating oxidative stress in an animal. The methods comprise administering to the animal a therapeutically effective amount of a combination of at least two of one or more unsaturated fatty acids (UFA); one or more nitric oxide releasing compounds (NORC); one or more anti-glycation agents; and colostrum.

The inventions are based upon the discovery that animals who were administered the compositions of the present invention demonstrated a significant improvement in immune function, learning and memory, balance, and muscle strength, and a significant reduction in oxidative stress in comparison to animals that were administered a control diet.

In various embodiments, the animal is any animal that has a need for ameliorating age related maladies, including but not limited to, enhancing and maintaining immune function, enhancing and maintaining cognitive function, enhancing and maintaining muscle strength, enhancing and maintaining balance, and reducing and mitigating oxidative stress. In one embodiment, the animal is a human or companion animal, preferably a canine or a feline. In another embodiment, the animal is an aging animal.

The UFA can be any UFA suitable for administration to an animal. UFAs can be obtained from any suitable source, synthetic or natural. Preferred sources of UFA are natural sources of such fatty acids and include, without limitation, primrose; dark green vegetables such as spinach; algae and blue-green algae such as spirulina; plant seeds and oils from plants such as flax, canola, soybean, walnut, pumpkin, safflower, sesame, wheat germ, sunflower, corn, and hemp; and fish such as salmon, tuna, mackerel, herring, sea bass, striped bass, halibut, catfish, sardines, shark, shrimp, and clams; and the extracted oils of any one or more of the foregoing. The UFA may also be synthetic, and as such may be produced according to any means suitable in the art, from any suitable starting material. The UFA may comprise a blend of any one or more UFA from any one or more sources, such as those exemplified above, whether natural or synthetic. In preferred embodiment the UFA comprises one or more of a natural fish oil, ALA, EPA, DPA, DHA, or another n-3 fatty acid from any source, more preferably fish oil.

In some embodiments, the UFAs are administered to the animal in amounts of from about 0.001 to about 1000 mg/kg/day, preferably from about 0.01 to 500, more preferably from about 0.1 to about 250. In other embodiments, the UFAs are administered to the animal in amounts of from about 0.001 to about 10 grams day, preferably from about 0.01 to 8, more preferably from about 0.12 to about 5.

The NORC can be any NORC suitable for administration. NORC can be obtained from any suitable source, synthetic or natural. In various embodiments, the NORC comprises arginine. Presently preferred sources of arginine include, without limitation, animal and plant proteins. Examples of plants considered rich in arginine content and suitable for use herein include, but are not limited to, legumes such as soy, lupins, and carob; grains such as wheat and rice; and fruits such as grapes. The rind of watermelon is a good natural source of citrulline. Seeds and nuts of plants such as cacao and peanut are also considered rich in arginine content and are therefore useful herein. Some examples of suitable animal proteins considered rich in arginine content are poultry and fish products. The NORC can also be synthetically produced, according to any suitable means in the art. As with UFA, the NORC content of any composition disclosed herein can include a blend of any natural or synthetic NORC. Both UFA and NORC, whether natural or synthetic, can be obtained directly or provided by a commercial source. In some embodiments, the NORC is arginine or a nitric oxide-releasing derivative thereof. In a preferred embodiment, the nitric oxide derivative is citrulline or ornithine, more preferably citrulline.

In some embodiments, the NORCs are administered to the animal in amounts of from about 0.001 to about 1000 mg/kg/day, preferably from about 0.01 to 500, more preferably from about 0.1 to about 250. In another embodiment, the NORCs are administered to the animal in amounts of from about 0.001 to about 10 grams day, preferably from about 0.01 to 8, more preferably from about 0.12 to about 5.

The anti-glycation agent can be any anti-glycation agent suitable for administration. In some embodiments, the anti-glycation agents are selected from the group consisting of carnosine, benfotiamine, pyridoxamine, alpha-lipoic acid, phenacyldimethylthiazolium chloride, taurine, aminoguanidine, resveratrol, and aspirin. In a preferred embodiment, the anti-glycation agent is alpha-lipoic acid.

In some embodiments, the anti-glycation agents are administered to the animal in amounts of from about 0.01 to about 1000 mg/kg/day, preferably from about 1 to 500, more preferably from about 10 to about 100. In another embodiment, the anti-glycation agents are administered to the animal in amounts of from about 0.001 to about 10 grams day, preferably from about 0.01 to 8, more preferably from about 0.1 to about 5.

Colostrum can be any colostrum suitable for administration to an animal. Colostrum can be obtained from any suitable source, synthetic or natural. Preferably, the colostrum is bovine colostrum.

In some embodiments, colostrum is administered to the animal in amounts of from about 0.01 to about 1000 mg/kg/day, preferably from about 1 to 500, more preferably from about 10 to about 100. In another embodiment, colostrum is administered to the animal in amounts of from about 0.001 to about 10 grams day, preferably from about 0.01 to 8, more preferably from about 0.1 to about 5.

In various embodiments, the compositions comprise a combination of at least two of one or more UFAs, one or more NORCs, one or more anti-glycation agents, and colostrum in a therapeutically effective amount. Generally, the compositions comprise from about 0.1 to about 50% UFA, from about 0.1 to about 20% NORC, from about 0.1 to about 20% anti-glycation agent, and from about 0.1 to about 20% colostrum. In various embodiments, the compositions comprise from about 1 to about 30% UFA, preferably from about 1 to about 15% UFA; from about 1 to about 15% NORC, preferably from about 1 to about 10% NORC; from about 1 to about 15% anti-glycation agent, preferably from about 1 to about 10% anti-glycation agent; and from about 1 to about 15% colostrum, preferably from about 1 to about 10% colostrum.

In one embodiment, the composition comprises at least two of fish oil, citrulline, alpha-lipoic acid, and bovine colostrum. In another embodiment, the composition comprises fish oil, citrulline, alpha-lipoic acid, and bovine colostrum.

In various embodiments, the compositions comprise from about 0.001 to about 1000 mg/kg/day of fish oil, preferably from about 0.01 to 500, more preferably from about 0.1 to about 250; from about 0.001 to about 1000 mg/kg/day of citrulline, preferably from about 0.01 to 500, more preferably from about 0.1 to about 250; from about 0.01 to about 1000 mg/kg/day of alpha-lipoic acid, preferably from about 1 to 500, more preferably from about 10 to about 100; and from 0.01 to about 1000 mg/kg/day of colostrum, preferably from about 1 to 500, more preferably from about 10 to about 100.

In the methods of the invention, compositions are administered to an animal in amounts of from about 0.005 to about 1000 mg/kg/day, preferably from about 0.01 to about 500 mg/kg/day, most preferably from about 0.05 to about 250 mg/kg/day.

Compositions of the present invention can be administered to the animal in any suitable form using any suitable administration route. For example, the compositions can be administered in a food composition, in a dietary supplement, in a pharmaceutical composition, in a nutraceutical composition, or as a medicament. Similarly, the compositions can be administered using a variety of administration routes, including oral, intranasal, intravenous, intramuscular, intragastric, transpyloric, subcutaneous, rectal, and the like. Preferably, the compositions are administered to an animal orally. Most preferably, the compositions are administered orally to an animal as a dietary supplement or as an ingredient in a food composition.

In a preferred embodiment, the compositions of the present invention are administered to an animal as an ingredient in a food composition suitable for consumption by an animal, including humans and companion animals such as dogs and cats. Such food compositions include complete foods intended to supply the necessary dietary requirements for an animal or food supplements such as animal treats.

In various embodiments, food compositions such as pet food compositions or pet treat compositions comprise from about 5% to about 50% crude protein. The crude protein material may comprise vegetable proteins such as soybean meal, soy protein concentrate, corn gluten meal, wheat gluten, cottonseed, and peanut meal, or animal proteins such as casein, albumin, and meat protein. Examples of meat protein useful herein include beef, pork, lamb, equine, poultry, fish, and mixtures thereof.

The food compositions may further comprise from about 5% to about 40% fat. Examples of suitable fats include animal fats and vegetable fats. Preferably, the fat source is an animal fat source such as tallow or grease. Vegetable oils such as corn oil, sunflower oil, safflower oil, rape seed oil, soy bean oil, olive oil and other oils rich in monounsaturated and polyunsaturated fatty acids, may also be used.

The food compositions may further comprise from about 10% to about 60% carbohydrate. Examples of suitable carbohydrates include grains or cereals such as rice, corn, millet, *sorghum*, alfalfa, barley, soybeans, canola, oats, wheat, rye, triticale and mixtures thereof. The compositions may also optionally comprise other materials such as dried whey and other dairy by-products.

The moisture content for such food compositions varies depending on the nature of the food composition. The food compositions may be dry compositions (e.g., kibble), semi-moist compositions, wet compositions, or any mixture thereof. In a preferred embodiment, the composition is a complete and nutritionally balanced pet food. In this embodiment, the pet food may be a "wet food", "dry food", or food of "intermediate moisture" content. "Wet food" describes pet food that is typically sold in cans or foil bags and has a moisture content typically in the range of about 70% to about 90%. "Dry food" describes pet food that is of a similar composition to wet food but contains a limited moisture content typically in the range of about 5% to about 15% or 20% (typically in the form or small biscuit-like kibbles). In one preferred embodiment, the compositions have moisture content from about 5% to about 20%. Dry food products include a variety of foods of various moisture contents, such that they are relatively shelf-stable and resistant to microbial or fungal deterioration or contamination. Also preferred are dry food compositions that are extruded food products such as pet foods or snack foods for either humans or companion animals.

The food compositions may also comprise one or more fiber sources. The term "fiber" includes all sources of "bulk" in the food whether digestible or indigestible, soluble or insoluble, fermentable or nonfermentable. Preferred fibers are from plant sources such as marine plants but microbial sources of fiber may also be used. A variety of soluble or insoluble fibers may be utilized, as will be known to those of ordinary skill in the art. The fiber source can be beet pulp (from sugar beet), gum arabic, gum talha, psyllium, rice bran, carob bean gum, citrus pulp, pectin, fructooligosaccharide, short chain oligofructose, mannanoligofructose, soy fiber, arabinogalactan, galactooligosaccharide, arabinoxylan, or mixtures thereof.

Alternatively, the fiber source can be a fermentable fiber. Fermentable fiber has previously been described to provide a benefit to the immune system of a companion animal. Fermentable fiber or other compositions known to skilled artisans that provide a prebiotic to enhance the growth of probiotics within the intestine may also be incorporated into the composition to aid in the enhancement of the benefit provided by the present invention to the immune system of an animal.

In some embodiments, the ash content of the food composition ranges from less than 1% to about 15%, preferably from about 5% to about 10%.

In a preferred embodiment, the composition is a food composition comprising and from about 15% to about 50% protein, from about 5% to about 40% fat, from about 5% to about 10% ash content, and having a moisture content of about 5% to about 20%. In other embodiments, the food composition further comprises prebiotics or probiotics as described herein.

When administered in a food composition, the amount of UFA as a percentage of the composition is from about 0.1 to about 40% of the food composition, preferably from about 3 to about 30%, more preferably from about 5 to about 20%. In various embodiments, food compositions comprise about 1%, 2%, 4%, 6%, 8%, 10%, 12%, 14%, 16%, 18%, 20%, 22%, 24%, 26%, 28%, 30%, 32%, 34%, 36%, 38%, or 40%.

When administered in a food composition, the amount of NORC as a percentage of the composition is from about 0.1 to about 40% of the food composition, preferably from about 3 to about 30%, more preferably from about 5 to about 20%. In various embodiments, food compositions comprise about 1%, 2%, 4%, 6%, 8%, 10%, 12%, 14%, 16%, 18%, 20%, 22%, 24%, 26%, 28%, 30%, 32%, 34%, 36%, 38%, or 40%.

When administered in a food composition, the amount of anti-glycation agent as a percentage of the composition is from about 0.1 to about 40% of the food composition, preferably from about 3 to about 30%, more preferably from about 5 to about 20%. In various embodiments, food compositions comprise about 1%, 2%, 4%, 6%, 8%, 10%, 12%, 14%, 16%, 18%, 20%, 22%, 24%, 26%, 28%, 30%, 32%, 34%, 36%, 38%, or 40%.

When administered in a food composition, the amount of colostrum as a percentage of the composition is from about 0.1 to about 40% of the food composition, preferably from about 3 to about 30%, more preferably from about 5 to about 20%. In various embodiments, food compositions comprise about 1%, 2%, 4%, 6%, 8%, 10%, 12%, 14%, 16%, 18%, 20%, 22%, 24%, 26%, 28%, 30%, 32%, 34%, 36%, 38%, or 40%.

In another embodiment, the compositions are administered to an animal in a dietary supplement. The dietary supplement can have any suitable form such as a gravy, drinking water, beverage, yogurt, powder, granule, paste, suspension, chew, morsel, treat, snack, pellet, pill, capsule, tablet, sachet, or any other suitable delivery form. The dietary supplement can comprise the compositions and optional compounds such as vitamins, preservatives, probiotics, prebiotics, and antioxidants. This permits the supplement to be administered to the animal in small amounts, or in the alternative, can be diluted before administration to an animal. The dietary supplement may require admixing with a food composition or with water or other diluent prior to administration to the animal. When administered in a dietary supplement, the compositions comprise from about 0.1 to about 90% of the supplement, preferably from about 3 to about 70%, more preferably from about 5 to about 60%.

In another embodiment, the compositions are administered to an animal in a pharmaceutical or nutraceutical composition. The pharmaceutical composition comprises the compositions of the present invention and one or more pharmaceutically or nutraceutically acceptable carriers, diluents, or excipients. Generally, pharmaceutical compositions are prepared by admixing a compound or composition with excipients, buffers, binders, plasticizers, colorants, diluents, compressing agents, lubricants, flavorants, moistening agents, and the like, including other ingredients known to skilled artisans to be useful for producing pharmaceuticals and formulating compositions that are suitable for administration to an animal as pharmaceuticals. When administered in a pharmaceutical or nutraceutical composition, the compositions comprise from about 0.1 to about 90% of the composition of the present invention, preferably from about 3 to about 70%, more preferably from about 5 to about 60%.

The compositions of the present invention can be administered to the animal on an as-needed, on an as-desired basis, or on a regular basis. A goal of administration on a regular basis is to provide the animal with a regular and consistent dose of the compositions or the direct or indirect metabolites that result from such ingestion. Such regular and consistent dosing will tend to create constant blood levels of the compositions and their direct or indirect metabolites. Thus, administration on a regular basis can be once monthly, once weekly, once daily, or more than once daily. Similarly, administration can be every other day, week, or month, every third day, week, or month, every fourth day, week, or month, and the like. Administration can be multiple times per day. When utilized as a supplement to ordinary dietetic requirements, the compositions may be administered directly to the animal, e.g., orally or otherwise. The compositions can alternatively be contacted with, or admixed with, daily feed or food, including a fluid, such as drinking water, or an intravenous connection for an animal that is receiving such treatment. Administration can also be carried out as part of a dietary regimen for an animal. For example, a dietary regimen may comprise causing the regular ingestion by the animal of the compositions in an amount effective to accomplish the methods of the present invention.

According to the methods of the invention, administration of the compositions, including administration as part of a dietary regimen, can span a period ranging from parturition through the adult life of the animal. In various embodiments, the animal is a human or companion animal such as a dog or cat. In certain embodiments, the animal is a young or growing animal. In more preferred embodiments, the animal is an aging animal. In other embodiments, administration begins, for example, on a regular or extended regular basis, when the animal has reached more than about 30%, 40%, or 50% of its projected or anticipated lifespan. In some embodiments, the animal has attained 40, 45, or 50% of its anticipated lifespan. In yet other embodiments, the animal is older having reached 60, 66, 70, 75, or 80% of its likely lifespan. A determination of lifespan may be based on actuarial tables, calculations, estimates, or the like, and may consider past, present, and future influences or factors that are known to positively or negatively affect lifespan. Consideration of species, gender, size, genetic factors, environmental factors and stressors, present and past health status, past and present nutritional status, stressors, and the like may also influence or be taken into consideration when determining lifespan.

The compositions of the present invention are administered to an animal for a time required to accomplish one or more objectives of the invention, e.g., ameliorating age related maladies; enhancing and maintaining immune function; enhancing and maintaining cognitive function; enhancing and maintaining muscle strength; enhancing and maintaining balance; reducing and mitigating oxidative stress; improving the quality of life; and promoting the health and wellness in an animal. Preferably, the compositions are administered to an animal on a regular basis.

In another aspect, the invention provides therapeutic compositions comprising the compositions of the present invention in a therapeutically effective amount for one or more of ameliorating age related maladies; enhancing and maintaining immune function; enhancing and maintaining cognitive function; enhancing and maintaining muscle strength; enhancing and maintaining balance; reducing and mitigating oxidative stress; improving the quality of life; and promoting the health and wellness in an animal. The therapeutic compositions contain the compositions of the present invention in amounts sufficient to administer the compositions of the present invention to an animal in amounts of from about 0.005 to about 1000 mg/kg/day, preferably from about 0.01 to about 500 mg/kg/day, most preferably from about 0.05 to about 250 mg/kg/day when the compositions are administered as anticipated or recommended for a particular composition. Typically, the compositions of the present invention comprise from about 1 to about 90% of a therapeutic composition, preferably from about 3 to about 70%, more preferably from about 5 to about 60%. In certain embodiments, the compositions of the present invention comprise over 90% of a therapeutic composition.

In various embodiments, the compositions further comprise one or more substances such as vitamins, minerals, probiotics, prebiotics, salts, and functional additives such as palatants, colorants, emulsifiers, and antimicrobial or other preservatives. Minerals that may be useful in such compositions include, for example, calcium, phosphorous, potassium, sodium, iron, chloride, boron, copper, zinc, magnesium, manganese, iodine, selenium, and the like. Examples of additional vitamins useful herein include such fat soluble vitamins as A, D, E, and K. Inulin, amino acids, enzymes, coenzymes, and the like may be useful to include in various embodiments.

In various embodiments, the compositions contain at least one of (1) one or more probiotics; (2) one or more inactivated probiotics; (3) one or more components of inactivated probiotics that promote health benefits similar to or the same as the probiotics, e.g., proteins, lipids, glycoproteins, and the like; (4) one or more prebiotics; and (5) combinations thereof. The probiotics or their components can be integrated into the compositions comprising the compositions (e.g., uniformly or non-uniformly distributed in the compositions) or applied to the compositions comprising the compositions (e.g., topically applied with or without a carrier). Such methods are known to skilled artisans, e.g., U.S. Pat. No. 5,968,569 and related patents.

Typical probiotics include, but are not limited to, probiotic strains selected from *Lactobacilli*, *Bifidobacteria*, or *Enterococci*, e.g., *Lactobacillus reuteri*, *Lactobacillus acidophilus*, *Lactobacillus animalis*, *Lactobacillus ruminis*, *Lactobacillus johnsonii*, *Lactobacillus casei*, *Lactobacillus paracasei*, *Lactobacillus rhamnosus*, *Lactobacillus fermentum*, and *Bifidobacterium* sp., *Enterococcus faecium* and *Enterococcus* sp. In some embodiments, the probiotic strain is selected from the group consisting of *Lactobacillus reuteri* (NCC2581; CNCM 1-2448), *Lactobacillus reuteri* (NCC2592; CNCM 1-2450), *Lactobacillus rhamnosus* (NCC2583; CNCM 1-2449), *Lactobacillus reuteri* (NCC2603; CNCM 1-2451), *Lactobacillus reuteri* (NCC2613; CNCM 1-2452), *Lactobacillus acidophilus* (NCC2628; CNCM 1-2453), *Bifidobacterium adolescentis* (e.g., NCC2627), *Bifidobacterium* sp. NCC2657 or *Enterococcus faecium* SF68 (NCIMB 10415). The compositions comprising the compositions of the present invention contain probiotics in amounts sufficient to supply from about $10^4$ to about $10^{12}$ cfu/animal/day, preferably from $10^5$ to about $10^{11}$ cfu/animal/day, most preferably from $10^7$ to $10^{10}$ cfu/animal/day. When the probiotics are killed or inactivated, the amount of killed or inactivated probiotics or their components should produce a similar beneficial effect as the live microorganisms. Many such probiotics and their benefits are known to skilled artisans, e.g., EP1213970B1, EP1143806B1, U.S. Pat. No. 7,189,390, EP1482811B1, EP1296565B1, and U.S. Pat. No. 6,929,793. In a preferred embodiment, the probiotic is *Enterococcus faecium* SF68 (NCIMB 10415). In one embodiment, the probiotics are encapsulated in a carrier using methods and materials known to skilled artisans.

As stated, the compositions may contain one or more prebiotics, e.g., fructo-oligosaccharides, gluco-oligosaccharides, galacto-oligosaccharides, isomalto-oligosaccharides, xylo-oligosaccharides, soybean oligosaccharides, lactosucrose, lactulose, and isomaltulose. In one embodiment, the prebiotic is chicory root, chicory root extract, inulin, or combinations thereof. Generally, prebiotics are administered in amounts sufficient to positively stimulate the healthy microflora in the gut and cause these "good" bacteria to reproduce. Typical amounts are from about one to about 10 grams per serving or from about 5% to about 40% of the recommended daily dietary fiber for an animal. The probiotics and prebiotics can be made part of the composition by any suitable means. Generally, the agents are mixed with the composition or applied to the surface of the composition, e.g., by sprinkling or spraying. When the agents are part of a kit, the agents can be admixed with other materials or in their own package. Typically, the food composition contains from about 0.1 to about 10% prebiotic, preferably from about 0.3 to about 7%, most preferably from about 0.5 to 5%, on a dry matter basis. The prebiotics can be integrated into the compositions using methods known to skilled artisans, e.g., U.S. Pat. No. 5,952,033.

A skilled artisan can determine the appropriate amount of the compositions, food ingredients, vitamins, minerals, probiotics, prebiotics, antioxidants, or other ingredients to be use to make a particular composition to be administered to a particular animal. Such artisan can consider the animal's species, age, size, weight, health, and the like in determining how best to formulate a particular composition and other ingredients. Other factors that may be considered include the type of composition (e.g., pet food composition versus dietary supplement), the desired dosage of each component, the average consumption of specific types of compositions by different animals (e.g., based on species, body weight, activity/energy demands, and the like), and the manufacturing requirements for the composition.

In a further aspect, the invention provides kits suitable for administering the compositions to animals. The kits comprise in separate containers in a single package or in separate containers in a virtual package, as appropriate for the kit component, the compositions and one or more of (1) one or more ingredients suitable for consumption by an animal; (2) instructions for how to combine the compositions and other kit components to produce a composition useful for ameliorating age related maladies, enhancing and maintaining immune function, enhancing and maintaining cognitive function, enhancing and maintaining muscle strength, enhancing and maintaining balance, and reducing and mitigating oxidative stress; (3) instructions for how to use the compositions useful for ameliorating age related maladies; (4) instructions for how to use the compositions useful for enhancing and maintaining immune function; (5) instructions for how to use the compositions useful for enhancing and maintaining cognitive function; (6) instructions for how to use the dietary formulations for enhancing and maintaining muscle strength; (7) instructions for how to use the dietary formulations for enhancing and maintaining balance; (8) instructions for how to use the dietary formulations for reducing and mitigating oxidative stress; (9) one or more probiotics; (10) one or more inactivated probiotics; (11) one or more components of inactivated probiotics that promote health benefits similar to or the same as the probiotics, e.g., proteins, lipids, glycoproteins, and the like; (12) one or more prebiotics; (13) a device for preparing or combining the kit components to produce a composition suitable for administration to an animal; and (14) a device for administering the combined or prepared kit components to an animal. In one embodiment, the composition is in a sachet.

When the kit comprises a virtual package, the kit is limited to instructions in a virtual environment in combination with one or more physical kit components. The kit contains the compositions and other components in amounts sufficient for ameliorating age related maladies, enhancing and maintaining immune function, enhancing and maintaining cognitive function, enhancing and maintaining muscle strength, enhancing and maintaining balance, and reducing and mitigating oxidative stress. Typically, the compositions and the other suitable kit components are admixed just prior to consumption by an animal. The kits may contain the kit components in any of various combinations and/or mixtures. In one embodiment, the kit contains a packet containing the compositions and a container of food for consumption by an animal. The kit may contain additional items such as a device for mixing the compositions and ingredients or a device for containing the admixture, e.g., a food bowl. In another embodiment, the compositions are mixed with additional nutritional supplements such as vitamins and minerals that promote good health in an animal. The components are each provided in separate containers in a single package or in mixtures of various components in different packages. In preferred embodiments, the kits comprise the compositions and one or more other ingredients suitable for consumption by an animal. Preferably such kits comprise instructions describing how to combine the compositions with the other ingredients to form a food composition for consumption by the animal, generally by mixing the compositions with the other ingredients or by applying the compositions to the other ingredients, e.g., by sprinkling the compositions on a food composition.

In a further aspect, the invention provides a means for communicating information about or instructions for one or more of (1) using the compositions useful for ameliorating age related maladies; (2) using the compositions useful for enhancing and maintaining immune function; (3); using the compositions useful for enhancing and maintaining cognitive function; (4) using compositions of the present invention for enhancing and maintaining muscle strength; (5) using compositions of the present invention for enhancing and maintaining balance; (6) using compositions of the present invention for reducing and mitigating oxidative stress; (7) admixing the composition or other components of the invention to produce a composition suitable for methods of the present invention; (8) contact information for consumers to use if they have a question regarding the methods and compositions of the invention; and (9) nutritional information about the compositions; wherein the composition comprises a combination of at least two of: one or more UFA; one or more NORC; one or more anti-glycation agents; and colostrum. The communication means is useful for instructing on the benefits of using the invention and communicating the approved methods for administering the compositions and food compositions containing the compositions to an animal. The means comprises one or more of a physical or electronic document, digital storage media, optical storage media, audio presentation, audiovisual display, or visual display containing the information or instructions. Preferably, the means is selected from the group consisting of a displayed website, a visual display kiosk, a brochure, a product label, a package insert, an advertisement, a handout, a public announcement, an audiotape, a videotape, a DVD, a CD-ROM, a computer readable chip, a computer readable card, a computer readable disk, a USB device, a FireWire device, a computer memory, and any combination thereof.

In another aspect, the invention provides methods for manufacturing a food composition comprising the compositions and one or more other ingredients suitable for consumption by an animal, e.g., one or more of protein, fat, carbohydrate, fiber, vitamins, minerals, probiotics, prebiotics, and the like. The methods comprise admixing one or more ingredients suitable for consumption by an animal with the compositions. Alternatively, the methods comprise applying the compositions alone or in conjunction or combination with other ingredients onto the food composition, e.g., as a coating or topping. The compositions can be added at any time during the manufacture and/or processing of the food composition. The composition can be made according to any method suitable in the art.

In another aspect, the invention provides a package useful for containing the compositions of the invention. The package comprises at least one material suitable for containing the compositions and a label affixed to the material containing a word or words, picture, design, acronym, slogan, phrase, or other device, or combination thereof, that indicates that the package contains the compositions with beneficial properties relating to age ameliorating age related maladies; enhancing and maintaining immune function; enhancing and maintaining cognitive function; enhancing and maintaining muscle strength; enhancing and maintaining balance; or reducing and mitigating oxidative stress. Typically, such device comprises the words "promoting healthy aging," "aging support," "senior support," "immune function support," "cognition support," or an equivalent expression printed on the material. Any package configuration and packaging material suitable for containing the compositions are useful in the invention, e.g., a bag, box, bottle, can, pouch, and the like manufactured from paper, plastic, foil, metal, and the like. In preferred embodiments, the package further comprises the compositions of the invention. In various embodiments, the package further comprises at least one window that permit the package contents to be viewed without opening the package. In some embodiments, the window is a transparent portion of the packaging material. In others, the window is a missing portion of the packaging material. In a preferred embodiment, the package contains a food composition adapted for a particular animal such as a human, canine, or feline, as appropriate for the label, preferably a companion animal food composition for dogs or cats. In a preferred embodiment, the package is a can or pouch comprising a food composition of the invention.

In another aspect, the invention provides for use of the compositions to prepare a medicament for one or more of ameliorating age related maladies; enhancing and maintaining immune function; enhancing and maintaining cognitive function; enhancing and maintaining muscle strength; enhancing and maintaining balance; reducing and mitigating oxidative stress; improving the quality of life; and promoting the health and wellness in an animal. Generally, medicaments are prepared by admixing a compound or composition, i.e., the compositions or a composition comprising the compositions, with excipients, buffers, binders, plasticizers, colorants, diluents, compressing agents, lubricants, flavorants, moistening agents, and other ingredients known to skilled artisans to be useful for producing medicaments and formulating medicaments that are suitable for administration to an animal.

EXAMPLES

The invention can be further illustrated by the following examples, although it will be understood that these examples are included merely for purposes of illustration and are not intended to limit the scope of the invention unless otherwise specifically indicated.

Diabetes mellitus was induced in sixty CD-1 mice. The mice were divided into two groups of thirty. Each group was administered either the control diet or the test diet for six weeks. The control diet was the American Institute of Nutrition purified diet formula for maintenance of mature rodents (AIN-93M). the AIN-93M diet contains 140 g/kg casein, 100 g/kg sucrose, 50 g/kg fiber, 155 g/kg dextrin, 466 g/kg corn starch, 35 g/kg standard salt mix, 40 g/kg soybean oil, 10 g/kg standard vitamin mix, 1.8 g/kg L-cystine and 2.5 g/kg choline chloride. The test diet was the AIN-93M supplemented with 80 mg/kg a lipoic acid, 100 mg/kg fish oil, 1.5 grams/kg bovine Colostrum, and 0.5 grams/kg citrulline. For each of the trials described below a randomly selected group of subset of mice from either group were tested.

The mice were maintained in an animal facility in a temperature-controlled room (22-25° C.) with twelve hour dark-light cycles. All rats had free access to laboratory chow and tap water during the acclamation period and to the control or test diet during the study period.

Example 1

Object Recognition Test

Mice were habituated to the apparatus, a 58×66×11 cm white plastic box, for three consecutive days before testing. Each mouse was allowed to freely explore the testing box for five minutes. On the first day of training, mice were placed in the testing apparatus with two identical objects (A and B), both with dimensions of 7×6.3×5.1 cm. On the second day, one of the original objects was removed and a new object (C) with dimensions of 8.2×3.8×7.4 cm added. Mice were placed in the testing apparatus for five minutes and the time each mouse spent sniffing or touching the new object was recorded. Results were expressed as the percentage of time spent investigating the new object.

Mice administered the test diet spent a greater amount of time investigating novel objects, suggesting a greater interest in their environment as compared to the mice administered the control diet. Results are shown in Table 1.

TABLE 1

| Animal ID | Control Diet | Test Diet |
|---|---|---|
| 1 | 50 | 67 |
| 2 | 18 | 73 |
| 3 | 52 | 61 |
| 4 | 62 | 56 |
| 5 | 33 | 79 |
| 6 | 57 | 65 |
| 7 | 25 | 50 |

TABLE 1-continued

| Animal ID | Control Diet | Test Diet |
|---|---|---|
| 8 | 88 | 43 |
| 9 | 30 | 83 |
| 10 | 33 | 82 |
| Average | 44.80 | 65.90 |

Example 2

T-Maze Learning Test

The T-maze is a hippocampal dependent reference learning task in which the animal integrates multiple cues in a novel environment to learn a new task. The T-maze consists of a black plastic alley with a start box at one end, two goal boxes at the other, and a guillotine door separating them with a treat in one of the arms. A block of training trials begins when a naive mouse is placed in the start box, the guillotine door is raised, a buzzer sounded. At the end of each trial, the mouse was returned to its home cage until the next trial. Mice were trained until they choose the correct arm. The number of trials to make one correct choice was the measure of acquisition.

Mice administered the test diet performed better in a T-maze test that measures how quickly mice learn spatial orientation. Mice administered test diets need far fewer trials to acquire spatial memory. Results are shown in Table 2.

TABLE 2

| Animal ID | Control Diet | Test Diet |
|---|---|---|
| 1 | 10 | 21 |
| 2 | 7 | 21 |
| 3 | 8 | 14 |
| 4 | 11 | 3 |
| 5 | 9 | 17 |
| 6 | 9 | 14 |
| 7 | 7 | 11 |
| 8 | 7 | 6 |
| 9 | 7 | 21 |
| 10 | 9 | 16 |
| 11 |  | 12 |
| 12 |  | 11 |
| Average | 8.40 | 13.92 |

Example 3

T-Maze Memory Test

Retention of the T-maze learning test was tested one week later by continuing training until the mice achieved the criterion of making five correct choices in six consecutive trials. The number of trials needed to reach this criterion was the measure of retention. This test reflects spatial memory.

Mice administered the test diet performed better in a T-maze test that measures how mice retain previously taught information. Mice administered the test diet needed far few tries to find the treat in a repeated test. Results are shown in Table 3.

TABLE 3

| Animal ID | Control Diet | Test Diet |
|---|---|---|
| 1 | 11 | 6 |
| 2 | 13 | 5 |

TABLE 3-continued

| Animal ID | Control Diet | Test Diet |
|---|---|---|
| 3 | 17 | 5 |
| 4 | 8 | 6 |
| 5 | 13 | 6 |
| 6 | 9 | 10 |
| 7 | 14 | 7 |
| 8 | 7 | 8 |
| 9 | 9 | 11 |
| 10 | 13 | 9 |
| Average | 11.40 | 7.30 |

Example 4

Pole Balancing Test

Mice were placed on a pole 0.25 inch in diameter 12 inches over a 0.75 inch foam and the time the mice balanced on the pole was recorded. The number of seconds mice can balance on a slowly rotating pole before falling is measured and reflects on motor function.

Mice administered the test diet were able to balance longer on the pole during the pole balancing test as compared to the mice administered the control diet, indicating that mice administered the test diet had significantly higher motor function as compared to mice administered the control diet. Results are shown in Table 4.

TABLE 4

| Animal ID | Control Diet | Test Diet |
|---|---|---|
| 1 | 53.67 | 180 |
| 2 | 79 | 154.67 |
| 3 | 74.67 | 180 |
| 4 | 4.67 | 150.33 |
| 5 | 14.33 | 10.67 |
| 6 | 68.67 | 180 |
| 7 | 20 | 180 |
| 8 | 37.33 | 122.67 |
| 9 | 37.67 | 134.67 |
| 10 | 20.67 | 180 |
| Average | 41.07 | 147.30 |

Example 5

Cage Hanging Test

Mice were allowed to grip the top of a wire mesh cage, which was then inverted 12 inches over a 0.75 inch foam pad. The time the mice were able to hang was recorded. The number of seconds mice can hang on to the ceiling of its cage before falling was measured and reflects on muscle strength.

Mice administered the test diet demonstrated significantly improved muscle strength. In the cage hanging test mice administered the test diet were able to hold on to the ceilings of their cages longer than the mice administered the control diet. Results are shown in Table 5.

TABLE 5

| Animal ID | Control Diet | Test Diet |
|---|---|---|
| 1 | 46.67 | 28.67 |
| 2 | 10 | 139.33 |

TABLE 5-continued

| Animal ID | Control Diet | Test Diet |
|---|---|---|
| 3 | 73 | 180 |
| 4 | 39 | 180 |
| 5 | 63 | 139 |
| 6 | 88.67 | 73 |
| 7 | 86.33 | 149 |
| 8 | 150 | 132 |
| 9 | 4 | 152.33 |
| 10 | 24.33 | 180 |
| Average | 58.50 | 135.33 |

Example 6

String Hanging Test

Mice gripped a string suspended 12 inches above a 0.75 inch foam pad. The number of seconds mice were able to hang on the string before falling was measured and reflects on muscle strength.

Mice administered the test diet were able to hang on longer to vertically suspended string than mice administered the control diet. Results are shown in Table 6.

TABLE 6

| Animal ID | Control Diet | Test Diet |
|---|---|---|
| 1 | 13.33 | 128.67 |
| 2 | 57.67 | 24 |
| 3 | 21 | 67.33 |
| 4 | 9.67 | 94 |
| 5 | 37 | 17 |
| 6 | 44.67 | 21.67 |
| 7 | 50.67 | 47.33 |
| 8 | 84.33 | 5.33 |
| 9 | 5 | 12.67 |
| 10 | 21 | 36 |
| Average | 34.43 | 45.40 |

Example 7

Glutathione Levels in Muscle Tissue

Glutathione (GSH) concentrations were determined by reverse phase HPLC by the method developed by Winters et al. Brain tissue samples were homogenized in serine-borate buffer [100 mM Tris.HCl, 10 mM boric acid, 5 mM L-serine, 1 mM DETAPAC (diethylenetriaminepentaacetic acid), pH 7.4] on ice, then derivatized with 1.0 mM NPM [N-(1-pyrenyl)-maleimide] in acetonitrile. Briefly, sufficient HPLC grade water was added to each sample to make a volume of 250 μL and 750 μL NPM (1 mM in acetonitrile). The mixture was incubated for five minutes at room temperature, then acidified with 2 N HCl. The derivatized samples were filtered through a 0.2-μm Acrodisc® filter (Advantec MFS, Inc., Dublin, Calif.) and injected onto a 5-μm C18 column in a reverse-phase HPLC system. The mobile phase was 70% acetonitrile and 30% water and was adjusted to a pH 2.5 through the addition of 1 mL/L of both acetic and o-phosphoric acids. The NPM derivatives were eluted from the column isocratically at a flow rate of 1 mL/min (34, 35). All sample quantitations were determined from standard curves using purified glutathione as described.

Mice administered the test diet significantly reduced oxidative stress in muscle. This is reflected in higher levels of glutathione GSH seen in the muscle tissue obtained from mice administered the test diet as compared to muscle tissue obtained from mice administered the control diet. Results are shown in Table 7.

TABLE 7

| Animal ID | Control Diet | Test Diet |
|---|---|---|
| 1 | 15.46 | 11.63 |
| 2 | 28.49 | 42.98 |
| 3 | 16.76 | 21.78 |
| 4 | 24.03 | 23.41 |
| 5 | 29.25 | 13.86 |
| 6 | 19.59 | 42.65 |
| 7 | 36.98 | 20.32 |
| 8 | 21.2 | 15.64 |
| 9 | 30.12 | 21.12 |
| 10 | 16.28 | 32.34 |
| 11 | 25.23 | 24.86 |
| 12 | 16.54 | 30.89 |
| 13 | 24.6 | |
| 14 | 19.66 | |
| 15 | 18.74 | |
| 16 | 28.35 | |
| 17 | 37.94 | |
| 18 | 19.47 | |
| Average | 23.82 | 25.12 |

Example 8

Glutathione Reductase (GR) Activity in Muscle Cells

GR activity was determined using a Colorimetric Assay for Glutathione Reductase, Bioxytech® GR-340 (OxisResearch Products, Percipio Biosciences, Inc., Foster City, Calif.).

Mice administered the test diet significantly reduced oxidative stress in muscle. This is reflected in higher levels of GR activity seen in the muscle tissue obtained from mice administered the test diet as compared to muscle tissue obtained from mice administered the control diet. Results are shown in Table 8.

TABLE 8

| Animal ID | Control Diet | Test Diet |
|---|---|---|
| 1 | 24.4 | 22.36 |
| 2 | 19.88 | 16.25 |
| 3 | 27.06 | 23.04 |
| 4 | 39.84 | 14.85 |
| 5 | 22.37 | 33.99 |
| 6 | 17.62 | 26.01 |
| 7 | 17.45 | 45.51 |
| 8 | 14.66 | 23.03 |
| 9 | 18.75 | 16.67 |
| 10 | 18.36 | 19.44 |
| 11 | 21.33 | 23.09 |
| 12 | 12.27 | 19.38 |
| 13 | 14.07 | |
| 14 | 18.92 | |
| 15 | 16.87 | |
| 16 | 13.49 | |
| 17 | 18.78 | |
| 18 | 12.35 | |
| Average | 19.36 | 23.64 |

Example 9

Gluatathione Peroxidase (GPx) Activity in Muscle Cells

GPx activity was determined by Colorimetric Assay for Cellular Glutathione Peroxidase, Bioxytech® cGPx-340

(OxisResearch Products, Percipio Biosciences, Inc., Foster City, Calif.). A cell sample was added to a solution containing GSSG, GR, and NADPH. The oxidation of NADPH to NADP+ is accompanied by a decrease in absorbance for 3 minutes at 340 nm and provides a spectrophotometric means for monitoring GPx enzyme activity following addition of 350 μL of tert-butyl hydroperoxide as the working substrate.

Mice administered the test diet significantly reduced oxidative stress in muscle. This is reflected in higher levels of glutathione peroxide GPx activity seen in the muscle tissue obtained from mice administered the test diet as compared to muscle tissue obtained from mice administered the control diet. Results are shown in Table 9.

TABLE 9

| Animal ID | Control Diet | Test Diet |
|---|---|---|
| 1 | 19.26 | 21.84 |
| 2 | 27.93 | 19.84 |
| 3 | 14.37 | 25.29 |
| 4 | 16.09 | 10.62 |
| 5 | 20.43 | 20.32 |
| 6 | 19.31 | 17 |
| 7 | 34.9 | 21.37 |
| 8 | 15.54 | 16.41 |
| 9 | 18.01 | 26.01 |
| 10 | 16.71 | 17.36 |
| 11 | 14.16 | 24.18 |
| 12 | 18.9 | 30.55 |
| 13 |  | 30.15 |
| 14 |  | 23.64 |
| 15 |  | 25.39 |
| 16 |  | 36.53 |
| 17 |  | 31.8 |
| 18 |  | 22.71 |
| Average | 19.63 | 23.39 |

Example 10

Glutathione Levels in Brain Tissue

Mice administered the test diet significantly reduced oxidative stress in brain tissue. This is reflected in higher levels of glutathione GSH seen in the brain tissue obtained from mice administered the test diet as compared to brain tissue obtained from mice administered the control diet. Results are shown in Table 10.

TABLE 10

| Animal ID | Control Diet | Test Diet |
|---|---|---|
| 1 | 51.99 | 60.13 |
| 2 | 59.44 | 61.44 |
| 3 | 71.32 | 59.32 |
| 4 | 63.75 | 52.33 |
| 5 | 56.54 | 53.63 |
| 6 | 51.2 | 57.54 |
| 7 | 52.01 | 60.21 |
| 8 | 49.81 | 69.5 |
| 9 | 59.53 | 69.03 |
| 10 | 82.83 | 52.96 |
| 11 | 48.25 | 66.45 |
| 12 | 53.21 | 69.15 |
| 13 | 49 | 60.94 |
| 14 | 45.47 | 63.32 |
| 15 | 46.63 | 59.31 |
| 16 | 52.61 | 43.9 |
| 17 | 49.98 | 51.44 |
| 18 | 45.96 | 70.17 |
| 19 | 56.4 | 65.27 |
| 20 | 55.49 |  |
| 21 | 41.1 |  |
| 22 | 49.94 |  |
| 23 | 50.56 |  |
| 24 | 54.07 |  |
| 25 | 30.16 |  |
| Average | 53.09 | 60.32 |

Example 11

Glutathione Reductase (GR) Activity in Brain Cells

Mice administered the test diet significantly reduced oxidative stress in brain tissue. This is reflected in higher levels of GR activity seen in the brain tissue obtained from mice administered the test diet as compared to brain tissue obtained from mice administered the control diet. Results are shown in Table 11.

TABLE 11

| Animal ID | Control Diet | Test Diet |
|---|---|---|
| 1 | 40.05 | 42.12 |
| 2 | 91.39 | 46.05 |
| 3 | 39.11 | 35.07 |
| 4 | 49.46 | 42.8 |
| 5 | 41.08 | 36.73 |
| 6 | 43.56 | 36.97 |
| 7 | 37.42 | 41.36 |
| 8 | 37.07 | 37.02 |
| 9 | 33.96 | 43.6 |
| 10 | 37.72 | 47.22 |
| 11 | 40.58 | 34.65 |
| 12 | 32.26 | 30.09 |
| 13 | 36.6 | 45.27 |
| 14 | 38.73 | 34.87 |
| 15 | 37.06 | 39.27 |
| 16 | 42.09 | 43.16 |
| 17 | 41.05 | 42.05 |
| 18 | 38.93 | 51.81 |
| 19 | 29.62 | 46.59 |
| 20 | 33.34 |  |
| 21 | 37.87 |  |
| 22 | 30.52 |  |
| 23 | 30 |  |
| 24 | 41.1 |  |
| 25 | 36.33 |  |
| Average | 39.88 | 40.88 |

Example 12

Glutathione Preoxidase (GPx) Activity in Brain Cells

Mice administered the test diet significantly reduced oxidative stress in brain tissue. This is reflected in higher levels of GPx activity seen in the brain tissue obtained from mice administered the test diet as compared to brain tissue obtained from mice administered the control diet. Results are shown in Table 12.

TABLE 12

| Animal ID | Control Diet | Test Diet |
|---|---|---|
| 1 | 55.79 | 46.18 |
| 2 | 101.3 | 45.38 |
| 3 | 49.07 | 43.51 |

TABLE 12-continued

| Animal ID | Control Diet | Test Diet |
|---|---|---|
| 4 | 54.16 | 46.21 |
| 5 | 41.4 | 47.75 |
| 6 | 57.47 | 33.17 |
| 7 | 50.17 | 46.04 |
| 8 | 43.68 | 45.82 |
| 9 | 46.99 | 46.83 |
| 10 | 48.43 | 48.53 |
| 11 | 49.82 | 42.72 |
| 12 | 47.09 | 41.19 |
| 13 | 46.81 | 43.84 |
| 14 | 45.96 | 39.67 |
| 15 | 65.41 | 51.38 |
| 16 | 48.83 | 42.5 |
| 17 | 53.27 | 47.67 |
| 18 | 38.98 | 59.81 |
| 19 | 43.71 | 54.18 |
| 20 | 51.04 | |
| 21 | 39.82 | |
| 22 | 31.83 | |
| 23 | 50.38 | |
| 24 | 61.35 | |
| 25 | 50.26 | |
| Average | 50.92 | 45.91 |

In the specification, there have been disclosed typical preferred embodiments of the invention. Although specific terms are employed, they are used in a generic and descriptive sense only and not for purposes of limitation. The scope of the invention is set forth in the claims. Obviously many modifications and variations of the invention are possible in light of the above teachings. It is therefore to be understood that within the scope of the appended claims the invention may be practiced otherwise than as specifically described.

What is claimed is:

1. A method for ameliorating age related maladies in a healthy animal comprising administering to the animal individually therapeutically effective amounts of:

one or more anti-glycation agents including alpha lipoic acid in an amount from about 1 to 500 mg/kg/day;

one or more UFA including fish oil in an amount from about 0.01 to 500 mg/kg/day;

one or more NORC including citrulline in an amount from about 0.001 to 10 g/kg/day; and colostrum in an amount from about 0.001 to 10 g/kg/day;

wherein the age related malady is loss of muscle strength or loss of balance.

2. The method of claim 1 wherein the UFA additionally comprises one or more of ALA, EPA, DPA, DHA, or another n-3 fatty acid from any source.

3. The method of claim 1 wherein the NORC additionally comprises arginine or a nitric oxide-releasing derivative thereof.

4. The method of claim 1 wherein the anti-glycation agent additionally comprising a member selected from the group consisting of carnosine, benfotiamine, pyridoxamine, phenacyldimethylthiazolium chloride, taurine, aminoguanidine, resveratrol, and aspirin.

5. The method of claim 1 wherein the fish oil is administered in an amount from about 0.1 to 250 mg/kg/day, citrulline is administered in an amount from about 0.12 to 5 g/kg/day, alpha lipoic acid is administered in an amount from about 10 to 100 mg/kg/day, and colostrum is administered in an amount from about 0.1 to 5 g/kg/day.

6. The method of claim 1 wherein the combination is formulated as a human food composition, pet food composition, or a dietary supplement.

7. The method of claim 1, wherein the age related malady is a loss of muscle strength.

8. The method of claim 1, wherein the age related malady is a loss of balance.

9. The method of claim 1, wherein the animal is a companion animal.

10. The method of claim 1, wherein the animal is a canine.

* * * * *